US006698428B2

United States Patent
Brain

(10) Patent No.: US 6,698,428 B2
(45) Date of Patent: Mar. 2, 2004

(54) ENDOTRACHEAL TUBE CONSTRUCTION

(76) Inventor: Archibald I. J. Brain, Sandford House, Fan Court Gardens, Longcross Rd., Chertsey, Surrey (GB), KT16 0DJ ( * ) Notice: Subject to any disclaimer, the term of this patent is extended or adjusted under 35 U.S.C. 154(b) by 0 days.

(21) Appl. No.: 09/827,225

(22) Filed: Apr. 5, 2001

(65) Prior Publication Data

US 2001/0018917 A1 Sep. 6, 2001

Related U.S. Application Data

(63) Continuation of application No. 09/560,529, filed on Apr. 27, 2000, which is a continuation of application No. 08/964,664, filed on Nov. 5, 1997, now Pat. No. 6,055,994.

(30) Foreign Application Priority Data

Nov. 6, 1996 (GB) .............................................. 9623060
Feb. 24, 1997 (GB) .............................................. 9703764

(51) Int. Cl.$^7$ ............................................ A61M 16/00
(52) U.S. Cl. .............................. 128/207.14; 128/207.15
(58) Field of Search ........................ 128/200.26, 207.14, 128/207.15

(56) References Cited

U.S. PATENT DOCUMENTS

| | | | | |
|---|---|---|---|---|
| 2,862,498 A | * | 12/1958 | Weekes .................. | 128/207.14 |
| 3,175,557 A | * | 3/1965 | Hammond ............. | 128/207.14 |
| 3,417,753 A | | 12/1968 | Mattler ........................ | 128/349 |
| 3,683,908 A | * | 8/1972 | Michael et al. ........ | 128/200.26 |
| 3,874,377 A | | 4/1975 | Davidson ............... | 128/207.15 |
| 3,880,168 A | * | 4/1975 | Berman .................. | 128/207.15 |
| 3,884,242 A | * | 5/1975 | Bazell et al. .......... | 128/207.15 |
| 3,968,800 A | * | 7/1976 | Vilasi .................... | 128/207.14 |
| 4,020,849 A | * | 5/1977 | Jackson ................. | 128/207.15 |
| 4,026,296 A | * | 5/1977 | Stoy et al. ............. | 128/207.15 |

(List continued on next page.)

FOREIGN PATENT DOCUMENTS

| | | | |
|---|---|---|---|
| CA | 2067782 | of 1989 | .......... A61M/16/04 |
| CA | 2141167 | of 1994 | .......... A61M/16/04 |
| EP | 0 402 872 A1 | of 1990 | ............ A61M/1/10 |
| EP | 0 533 371 B1 | of 1993 | .......... A61M/16/04 |
| EP | 0 533 371 A1 | of 1993 | .......... A61M/16/04 |

(List continued on next page.)

OTHER PUBLICATIONS

Willis et al., "Tracheal tube cuff pressure–Clinical use of the Cardiff Cuff Controller", *Anaesthesia*, 43:312–314, 1988.
Patel et al., "Tracheal tube cuff pressure–Chages during nitrous oxide anaesthesia following inflaton of cuffs with air and saline", *Anaesthesia*, 39:862–864, 1984.

(List continued on next page.)

*Primary Examiner*—Aaron J. Lewis
(74) *Attorney, Agent, or Firm*—Hale and Dorr LLP

(57) ABSTRACT

In its presently preferred form, an endotracheal tube (ET) is shaped to bring its rounded or bevelled distal tip end into the central axis or midline, for ease of passage into the glottic opening and through the region of the vocal cords; the distal-end shaping also involves a laterally and vertically reducing taper that is symmetrical with respect to a vertical plane of symmetry which includes the central axis. Distal-end ports or perforations are in the symmetrically arrayed walls of a triangular section of the tube which at least characterizes the region of tapering section and which conforms with the triangular-shaped space between the vocal cords, for added ease of insertion into the patient's trachea. The reducing taper of the roughly triangular-shaped section extends preferably and optionally to form a wedging fit against vocal cords, with or without the assistance of a conventional inflatable cuff of similar sectional profile.

9 Claims, 4 Drawing Sheets

U.S. PATENT DOCUMENTS

| | | | |
|---|---|---|---|
| 4,056,104 A | * 11/1977 | Jaffe | 128/207.15 |
| 4,116,201 A | * 9/1978 | Shah | 128/207.15 |
| 4,156,428 A | * 5/1979 | Henkin | 128/207.15 |
| 4,210,478 A | 7/1980 | Shoney | 156/242 |
| 4,235,239 A | * 11/1980 | Elam | 128/207.15 |
| 4,324,235 A | * 4/1982 | Beran | 128/207.15 |
| 4,402,684 A | * 9/1983 | Jessup | 128/207.14 |
| 4,446,864 A | 5/1984 | Watson et al. | 128/207.14 |
| 4,488,548 A | * 12/1984 | Agdanowski | 128/207.15 |
| 4,538,606 A | * 9/1985 | Whited | 128/207.15 |
| 4,798,597 A | 1/1989 | Vailancourt | 604/270 |
| 4,848,331 A | 7/1989 | Northway-Meyer | 128/200.26 |
| 4,953,547 A | 9/1990 | Poole, Jr. | 128/203.12 |
| 4,960,122 A | * 10/1990 | Mizus | 128/207.14 |
| 4,976,261 A | 12/1990 | Ginek et al. | 128/207.15 |
| 5,038,766 A | 8/1991 | Parker | 128/200.26 |
| 5,060,647 A | * 10/1991 | Alessi | 128/207.14 |
| 5,285,778 A | 2/1994 | Mackin | 28/207.15 |
| 5,303,697 A | * 4/1994 | Brain | 128/200.26 |
| 5,334,148 A | * 8/1994 | Martin | 604/96.01 |
| 5,339,805 A | 8/1994 | Parker | 128/200.26 |
| 5,339,808 A | 8/1994 | Don Michael | 128/207.15 |
| 5,372,131 A | * 12/1994 | Heinen, Jr. | 128/207.15 |
| 5,507,284 A | * 4/1996 | Daneshvar | 128/207.14 |
| 5,569,219 A | 10/1996 | Hakki et al. | 604/282 |
| 5,865,176 A | 2/1999 | O'Neil | 128/207.15 |
| 5,915,383 A | 6/1999 | Pagan | 128/207.15 |
| 6,012,452 A | * 1/2000 | Pagan | 128/200.26 |
| 6,055,984 A | * 5/2000 | Brain | 128/207.14 |

FOREIGN PATENT DOCUMENTS

| | | | |
|---|---|---|---|
| GB | 1 288 033 | of 1972 | A61M/1/00 |
| GB | 2 008 140 A | of 1979 | A61M/25/00 |
| JP | 10118181 A | of 1998 | A61M/16/04 |
| JP | 10295715 A | of 1998 | A61M/16/04 |
| JP | 10295816 A | of 1998 | A61M/16/04 |
| WO | WO 91/03207 | of 1991 | A61B/17/36 |
| WO | WO 91/07201 | of 1991 | A61M/12/04 |
| WO | WO 91/12845 | 9/1991 | |
| WO | WO 98/23317 | of 1998 | A61M/16/04 |

OTHER PUBLICATIONS

Pippin et al., "Long–term tracheal intubation practice in the United Kingdom", *Anaesthesia*, 38:791–795, 1983.

EPO Communication and attached European Search Report, Applicataion No. EP 97 30 8918, EPO Communication dated Sep. 22, 1998, 4 pages.

Raeder et al., "Tracheal tube cuff pressures", *Anaesthesia*, 40:444–447, 1985.

Seegobin et al., "Endotracheal cuff pressure and tracheal mucosal blood flow:endoscopic study of effects of four large volume cuffs", British Medical Journal, 288:965–968, Mar. 1984.

Bernhard et al., "Physical Characteristics of and Rates of Nitrous Oxide Diffusion into Tracheal Tube Cuffs", *Anaesthesiology*, 48:413–417, 1978.

"Clinical Reports", *Anaesthesiology*, vol. 50, No. 4, Apr. 1979.

"Prevention of Hospital–Acquired Pneumonia: Measuring Effect in Ounces, Pounds, and Tons", *Annals of Internal Medicine*, vol. 122, No. 3, Feb. 1995.

Lindholm, "Prolonged Endotracheal Intubation", ACTA *Anaesthesiologica Scandinavica*, pp. 32–46, 1969.

Miller, "A pressure regulator for the cuff of a tracheal tube", *Anaesthesia*, 47:594–596, 1992.

* cited by examiner

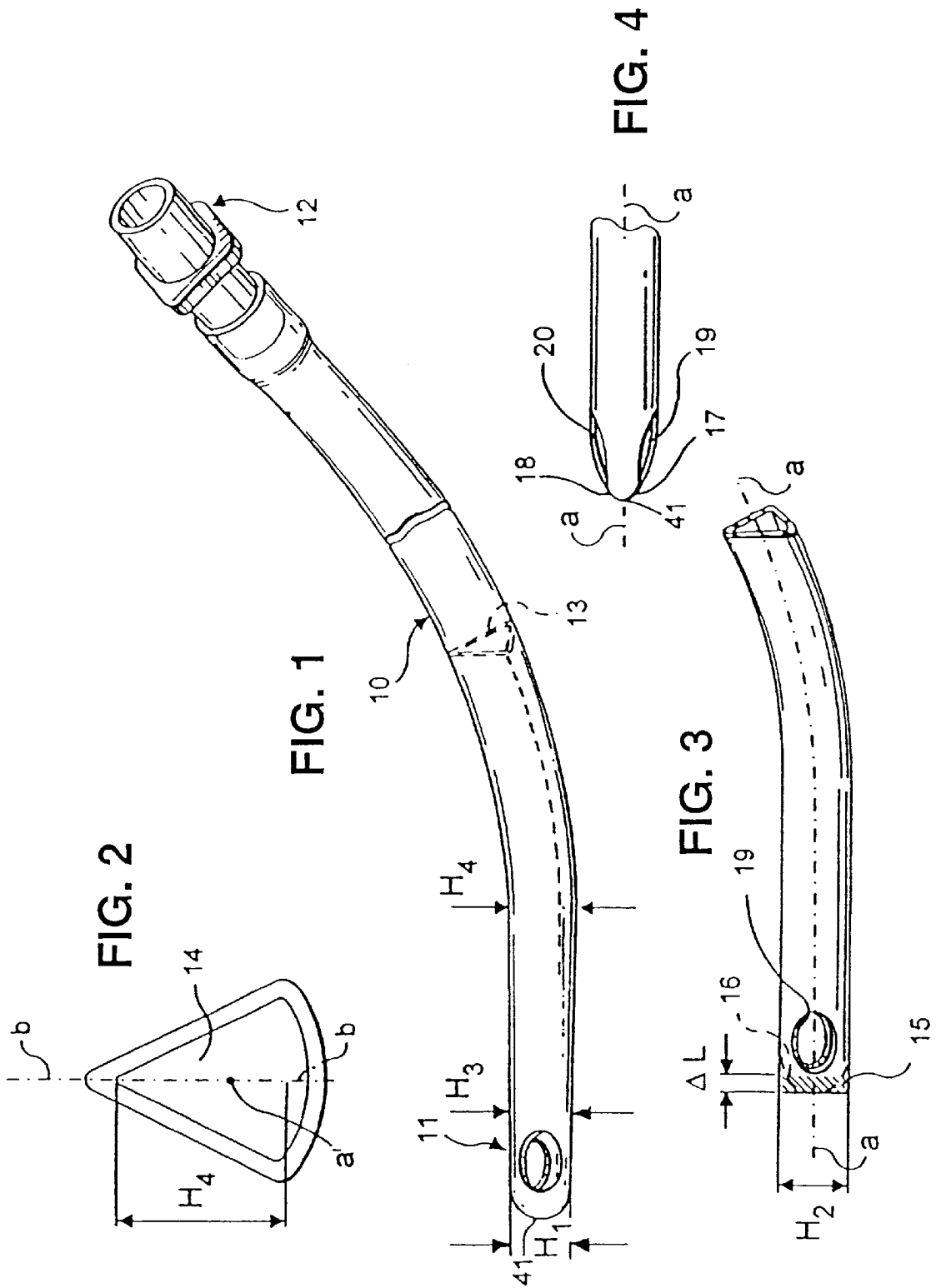

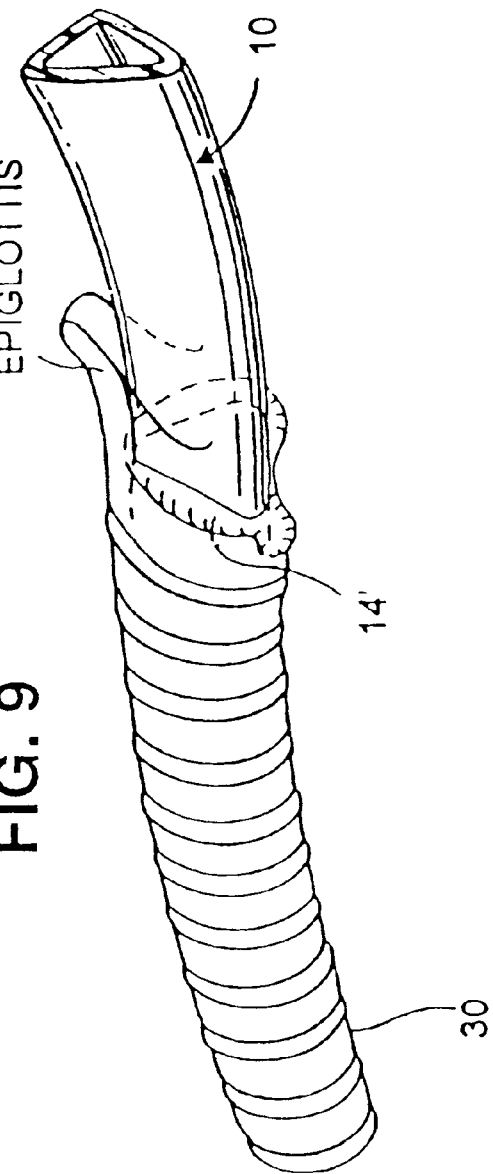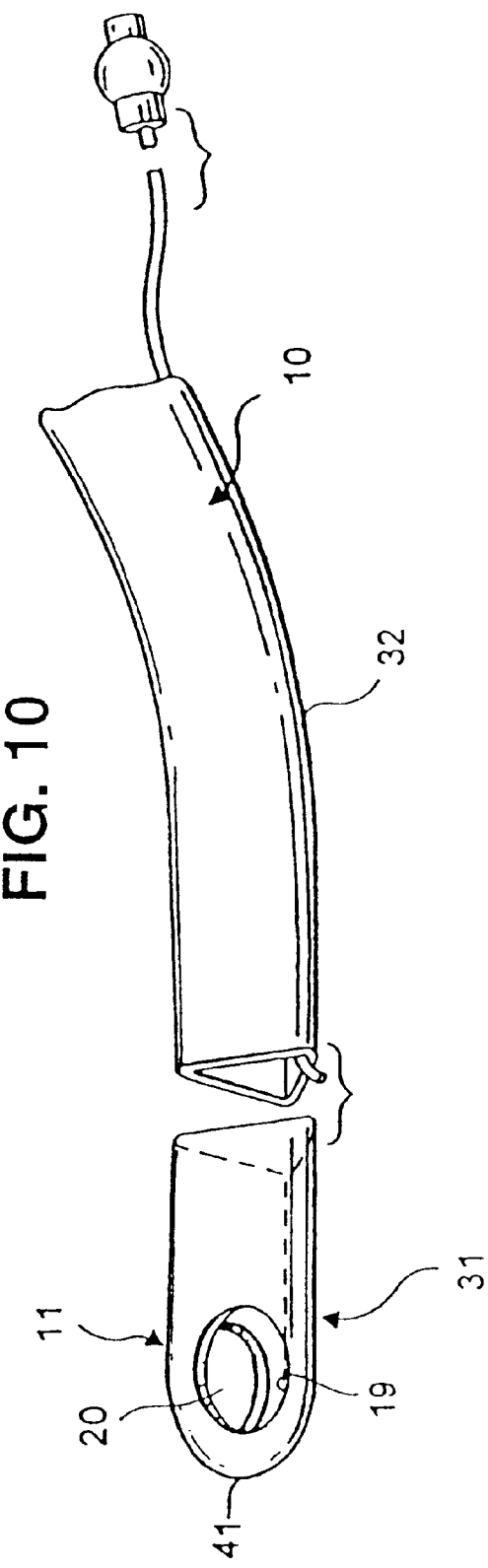

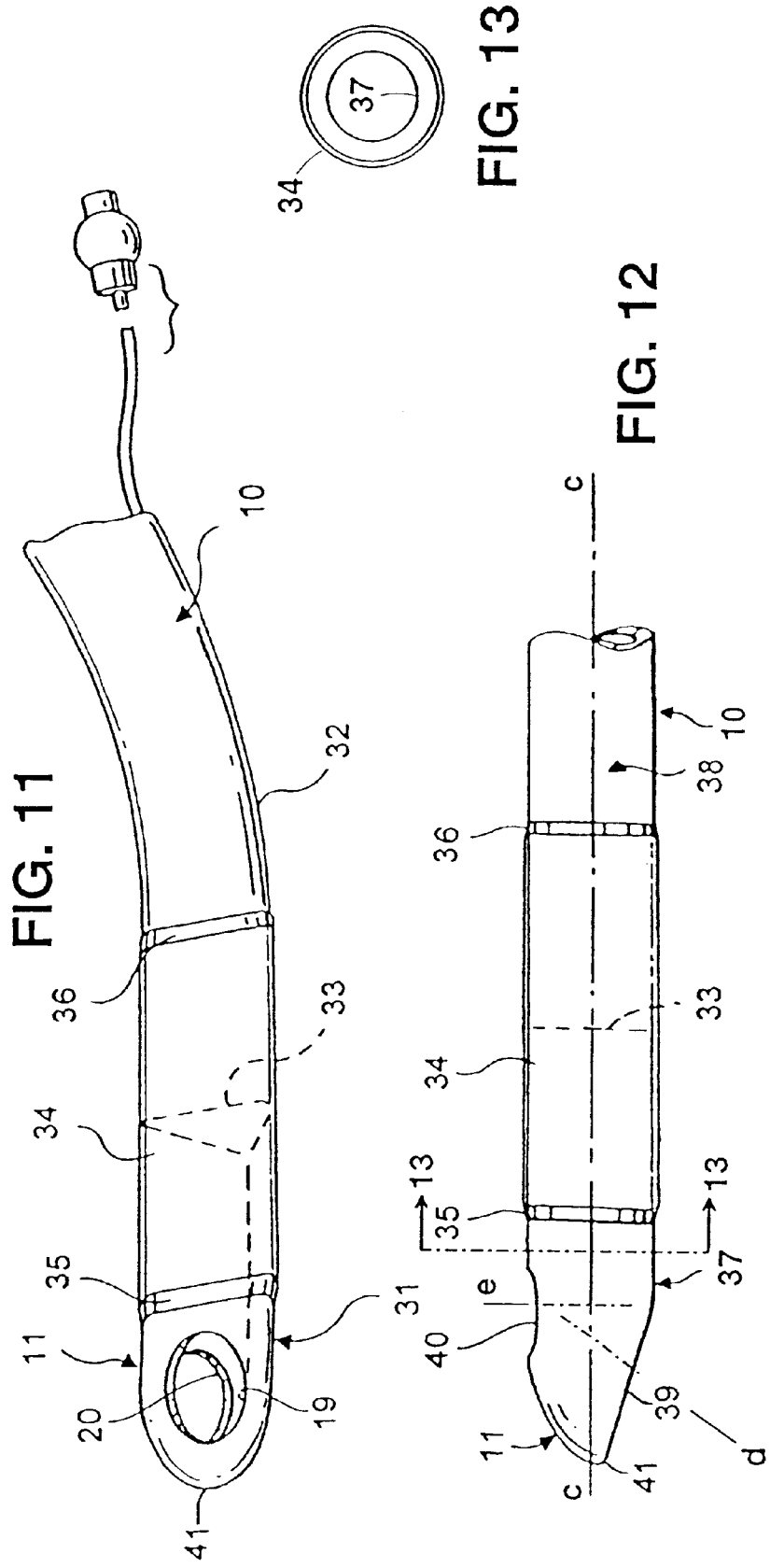

ENDOTRACHEAL TUBE CONSTRUCTION

CROSS-REFERENCE TO RELATED APPLICATION

This application is a continuation of U.S. patent application Ser. No. 09/560,529 filed on Apr. 27, 2000, which is a continuation of Ser. No. 08/964,664 filed Nov. 5, 1997, now U.S. Pat. No. 6,055,994, which claims priority to U.K. application No. 9703764.2 filed on Feb. 24, 1997 and U.K. 9623060.2 filed on Nov. 6, 1996.

BACKGROUND OF THE INVENTION

The endotracheal tube is an artificial airway device usually made of plastics or rubber material which consists of a flexible, usually somewhat curved tube, typically of 8-mm internal diameter in adults, with a square-cut outer or proximal end for attachment to a standard 15-mm connector and a bevelled or diagonally-cut opposite or distal end for ease of insertion through the laryngeal aperture (glottis) and into the trachea (windpipe). Normally, an endotracheal tube has hermetically sealed engagement to the walls of the trachea, by reason of a typically cylindrical or spheroidal concentric plastic or rubber cuff fitted to the tube shaft, at some 2 to 3 cm of proximal offset from said bevelled end. Such a cuff is inflated by means of an inflating syringe via an inflation line commonly running in the wall of said tube and continuous with a flexible pilot tube, pilot balloon and spring-loaded check valve; after the endotracheal tube has been installed to the correct depth in the patient's trachea, the cuff is inflated, and the check valve retains the cuff in its inflated state.

A wide variety of such endotracheal tubes are known and in common use throughout the world, and most have in common the features detailed above. Their popularity is due to their ability to provide means of administering anaesthetic gases to the patient's lungs while simultaneously preventing entry into the lungs of potentially lethal gastric juice which may otherwise flood into the airways when the body's protective reflexes have been abolished by the administration of general anaesthesia. However, many complications are known to be caused by the placement of such tubes, whether from trauma of insertion, pressure of the tube lying against the walls of the larynx or pressure exerted on the delicate walls of the trachea by the sealing cuff once inflated. The traditional bevel on an endotracheal tube is in no way designed to fit the slot-shaped and somewhat triangular aperture it must pass through when the tube is inserted, resulting commonly in injury to the larynx due to the bevel tip bruising one or the other side of the larynx during passage. Also, once installed, the circular cross-section of conventional tubes differs from the roughly triangular slotted shape of the laryngeal aperture so that when the vocal cords forming the sidewalls of said triangle contract against this circular shape, stretching and consequent malfunction of the cords commonly occurs. Tubes have been designed, for example some designs of plastic (PVC) tube manufactured by Mallinkrodt (Germany and USA) in which the bevelled tip is directed away from the tube's side wall, but such tube-bevel design does not bring the leading edge of the bevel into the mid-line of the tube shaft, and the tube is of uniform hardness (typically 80 durometer).

To insert an endotracheal tube in a patient's windpipe, an instrument called a laryngoscope is normally used. This device comprises a light source placed within a blade designed to lift the tongue forwards, revealing the glottic aperture below the posterior surface of the tongue. Endotracheal tubes are normally curved so as to facilitate entry of the bevelled tube tip between the vocal cords once these have been revealed by the laryngoscope. However, this curvature of the tube, while facilitating entry into the glottis, actually causes the tube to scrape against the anterior wall of the windpipe as it passes further into place, because the anatomy of the windpipe curves in the direction opposite to the curvature of the tube. My pending patent application Ser. No. 08/901,055 describes an intubating laryngeal mask, namely, an LMA modified to act as a guide to installing an endotracheal tube; wherein the need to use a laryngoscope can be avoided, while also avoiding the need for the endotracheal tube to be curved. The present invention pertains to an endotracheal tube designed principally for use with an intubating LMA, and the disclosure of said pending patent application is hereby incorporated by reference.

BRIEF STATEMENT OF THE INVENTION

The principal object of the invention is to provide an improved endotracheal tube construction, featuring ease of entry into the glottic opening.

A specific object is to meet the above object with a distal-end configuration which substantially conforms to the sectional profile of the glottic opening.

Another specific object is to meet the above objects with a distal-end element of lesser durometer than that of a conventional endotracheal tube, said element having a proximal end configured for fixed connection to the distal end of a conventional endotracheal tube, and said element having a distal end which is configured for substantial conformance to the sectional profile of the glottic opening.

It is also an object to meet the above objects with an endotracheal tube having a sectional profile which not only conforms at its distal end to the profile of the glottic opening but which also conforms to said profile continuously in the proximal direction, at least to a location of potentially lapped registry with the vocal cords of a patient, in the installed position of the endotracheal tube.

Still another object is to provide an endotracheal tube with a distal-end section adapted for installed sealing conformance to tissues of the vocal-cord region.

Yet another object is to provide an endotracheal tube of the character indicated with a distal end which incorporates radio-opaque means for radiographic identification of installed location in a patient's trachea.

In its preferred embodiment, the invention achieves these objects, along with further features to be described, by providing an endotracheal-tube (ET) construction which is adapted for use with an intubating laryngeal-mask airway (LMA) and wherein the distal end of the ET tube per se is specially formed for ease of entry into a patient's glottic opening. Preferably, at least the distal end of the new ET construction is of elastomeric material (a) that is of less-than-conventional stiffness, for softer and somewhat yielding entry engagement with the glottic opening, (b) that is smoothly and symmetrically formed with narrow width about a vertical plane of symmetry which includes what may be termed the tube axis, as said axis may be said to exist in close approach to the distal end, (c) that progressively broadens in the proximal direction from said end, into a generally triangular section which conforms to the profile of the glottic opening and which is also adapted for sealing or near-sealed relation to the vocal cords, and (d) that, at least for that portion of the distal length of the ET tube which extends from the glottic opening into lapped engagement with the vocal cords, the generally triangular section progressively reduces to the extent of establishing a progressive and effectively sealed closing engagement with the walls of the vocal cords.

Various embodiments are described.

DESCRIPTION OF THE DRAWINGS

In the drawings which show, for illustrative purposes, preferred and other embodiments of the invention:

FIG. 1 is a side view, partially in elevation and partially in perspective, of a preferred endotracheal-tube embodiment of the invention;

FIG. 2 is a front-aspect view, schematically indicative of the shape of a glottic opening;

FIG. 3 is a fragmentary side-aspect view similar to FIG. 1, to illustrate manufacturing steps in fabricating the distal end portion of the endotracheal tube of FIG. 1;

FIG. 4 is an enlarged fragmentary plan view of air/gas porting adjacent the distal end of the endotracheal tube of FIG. 1;

FIG. 9 is a view in perspective to show insertional accommodation of the distal end of an endotracheal tube of FIG. 1 or FIG. 8 in a human trachea, the trachea being schematically featured essentially only by its cartilagineous bands;

FIG. 10 is a side view in partial perspective, showing separate component parts of a modified distal-end construction;

FIG. 11 is a view similar to FIG. 10, to shown an assembled distal end, for the component parts of FIG. 10; and FIG. 12 is a fragmentary distal-end view in side elevation for a further embodiment of the invention FIG. 13 is a sectional view of FIG. 12 taken in the plane 13–13 of FIG. 12 showing the cylindrical cross-section of the distal component of the endotracheal tube.

DETAILED DESCRIPTION

Figure 5:
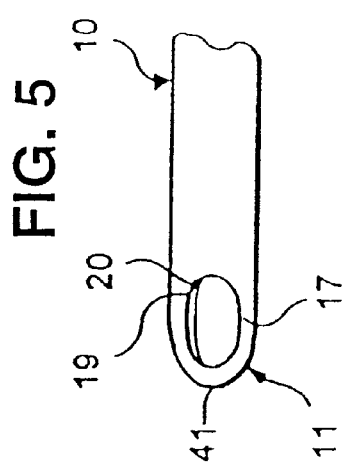
FIG. 5 is an enlarged fragmentary side view of the distal end of FIG. 4.

FIG. 1 illustrates the currently preferred endotracheal tube (ET) of the invention, and is seen to comprise an elongate flexible tube 10, which may have an initial curvature, between a distal end 11 and a proximal end fitting 12 that is adapted for external connection to conventional gas/air-monitoring and supply equipment available to the anaesthetist The mention of curvature between ends 11, 12 is primarily for purposes of having the ET of FIG. 1 be recognized as an ET, because the thinking and practices of anesthetists have long been conditioned by conventional ET devices as having an arcuate appearance; moreover, the arcuate configuration shown can be understood as an arc in a single vertical plane of symmetry, which includes a geometrically central axis, designated a—a in FIG. 4.

As suggested above, it is recommended that the device of FIG. 1 be inserted via an installed intubating LMA, as of the presently preferred rigid-airway nature described in pending application Ser. No. 08/901,055, wherein the total angle of airway bend, is a circular arc of preferably 128 to 131 degrees, between a straight proximal end and a distal ET-launching end, which aims the launched distal end of an ET for short-span directed entry into a patient's glottic opening.

It is a feature of the invention that at least the distal-end portion of the ET of FIG. 1 shall be of generally isosceles-triangular section 13 which converges gradually from a maximum geometric altitude $H_4$ to a reduced intermediate altitude $H_3$, and distally ending with a most-reduced altitude $H_1$; and these triangle altitudes are to be understood in the context of the patient's glottic opening 14 (FIG. 2) having an altitude $H_4$ which is the maximum external altitude of the generally triangular section of ET tube 10, it being noted that the altitude $H_4$ in FIG. 2 substantially coincides with a vertical plane b-b of symmetry of the glottic opening 14, and that this plane b-b of symmetry includes what may be identified as the longitudinally central mid-line or axis a' of the glottic opening. It is also noted, as in FIG. 2, that the term "generally isosceles" applies to the substantial equality of the oppositely inclined sidewalls of the glottic opening but that the third or base side is bowed; as seen in FIG. 2 and also in the frontal aspect profile of FIG. 7. The context for distal-end 11 entry into the patient's glottic opening 14 is therefore one of relatively safe clearance, and thus tolerance for a range of safely directed ET entry into the glottic opening.

The indicated tolerance is aided favorably in terms of avoiding trauma-inducing ET engagement with body tissues in the intubating course of LMA-guided entry into the glottic opening. For example, it is a feature of the invention that the stiffness/hardness of the material of at least the glottis-entering distal end of ET tube 10 shall be materially reduced from the typically 80-durometer hardness which characterizes currently favored ET constructions of constant circular section. In contrast to such conventional practice, the texture of the elastomeric material of the glottis-entering end of tube 10 is substantially softer, e.g., in the range of 55 to 65 durometer, and preferably of 60-durometer hardness.

A further feature of the invention, particularly for enhanced avoidance of trauma upon ET insertional advance into and through the glottic opening, derives from my originally preferred technique of distal-end manufacture. This technique of distal-end formation is illustrated in FIG. 3, wherein a distal increment ΔL of length is laterally crushed and bonded into substantially flat local conformance with and adoption of the defined vertical plane of symmetry (i.e., a—a in FIG. 4). The crush action necessarily establishes a crushed and bonded closure of the distal end of the ET tube, which in the case of a circular tube will become a diametrical closure of substantially uniform thickness (and vertical extent $H_2 > H_1$), and which in the case of the preferred generally triangular section 13 may become a closure that is of more wedge-shaped section, but symmetrical about the above-noted central vertical plane of symmetry. In FIG. 3, the crushed closure of the distal end of tube 10 is designated by shading 15, and a dashed profile 16 will be understood to suggest a finishing step of abrading or otherwise reducing the distal end of tube 10 to a smoothly rounded finish which is substantially as collectively shown by the distal-end profiles of FIGS. 1, 3, 4, 5 and 7.

The flattened, sealed and rounded distal end 11 will be seen to extend distally forward of the minimum section altitude $H_1$ and to have been reduced from the flattened span $H_2$ which preceded the rounding step. From this flattened, and now also rounded, distal end 11, the opposed sidewalls 17, 18 are seen in FIG. 4 to spread in progressive definition of the intermediate generally triangular-section dimensions which are characterized by the intermediate altitude $H_3$, and with further progressive section enlargement to a maximum altitude $H_4$ of generally triangular-section magnitude, namely at the location of substantial triangular-section conformance to the profile (FIG. 2) of the glottic opening 14. In close adjacency to the distal end, the diverging sidewalls 17, 18 are shown with symmetrically opposed ports in the form of longitudinally elongate oval openings 19, 20 that are best seen in FIGS. 4, 6 and 7, it being noted that in the region between altitudes $H_3$ and $H_4$, the symmetrically opposed walls 17, 18 will have become components of flat surfaces that are adapted for substantial if not total conformance to contacted divergent inner faces of the vocal cords.

Figure 6:
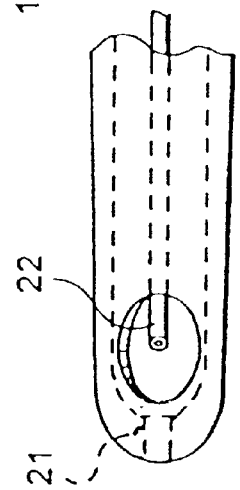
FIG. 6 is an end view of the distal end of the endotracheal tube of FIGS. 1 and 4, with modification to provide centralizing guidance of a fiber-optic viewing/illuminating device.
Figure 7:
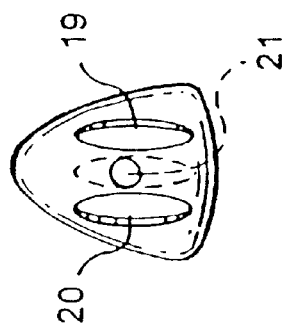
FIG. 7 is a view similar to FIG. 5, but additionally showing the FIG. 6 provision for centralizing guidance.

FIGS. 6 and 7 serve to illustrate that for those who prefer the assurance of optical-fiber illumination and fiberscope distally directional viewing on the local central axis of the distal end 11, a short central bore 21 in the otherwise closed end 11 will serve to stabilize axially central orientation of optical-fiber means 22 inserted via the generally triangular-section passage within ET tube 10. FIG. 7 further shows inner-wall ramp profiling 22', convergent to bore 21, whereby to deflect the distal end of the optical-fiber means 22 into smooth alignment with and guided entry into the central bore 21.

Figure 8:
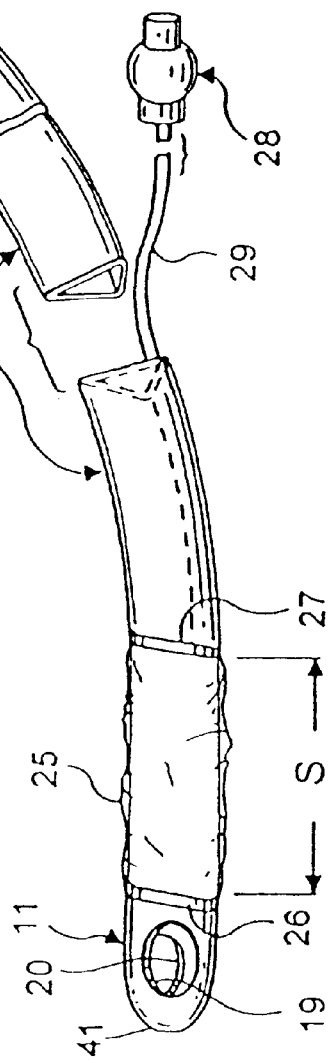
FIG. 8 is a view similar to FIG. 1 to show a modification.

The ET device of FIG. 8 incorporates a modification from the device of FIG. 1, involving a circumferentially continuous sleeve 25 of flexible plastic, peripherally sealed, in longitudinally spaced relation S, between such seals at 26/27 that are designed to fully lap the vocal cords. And inflation/deflation means such as a manually operated piston/cylinder syringe (not shown) will be understood, when connected to a suitable check valve 28, to serve inflation air via flexible means 29 which communicates within tube 10 to the closed volume external to tube 10 but contained within the described flexible sleeve 25. Upon ET tube 10 insertion into and via a patient's glottic opening 14, to the extent of sleeve-25 overlap with the patient's vocal cords, the sealed efficacy of full engagement with the vocal cords is assured by relatively light-pressure inflation of the sleeve via means 28, 29.

FIG. 9 serves as a schematic illustration of trachea reception of either one of the described ET embodiments. It is noted that the angle between the laryngeal inlet and the substantially straight trachea is the reverse of curvature developed or necessitated by laryngoscope-guided curvature of ET passage to the point 14' of glottic-aperture entry.

FIGS. 10 and 11 are respectively illustrative of separate ET components of the same device, namely a distal-end component 31 and a proximal tube component 32, which may integrally extend to a proximal end (not shown) that may be as described for the proximal end means 12 of FIG. 1. The adjacent ends of components 31, 32 confront each other with compatibly matched sectional profiles, which suitably are butt-welded with full peripheral completion of their welded relation, suggested at 33 in FIG. 11. A sleeve 34 of flexible material is seen in FIG. 11 to straddle weld 33 and to be in circumferentially complete bonded connection at its respective ends 35, 36 to the external surface of each of the respective components 31, 32. Optionally, inflation/deflation means, as at 28, 29 in FIG. 8 is provided for sleeve 34 action, but the additional function provided by sleeve 34 is a safety feature, namely, in case of an inadvertent failure of the weld connection 33 while the ET device is installed in a patient. Specifically, in such an unfortunate circumstance, the sleeve 34 provides a longitudinal tie of the severed component connection, and the tie enables safe extraction of the severed parts in a single extracting retraction.

It will be seen that the embodiment of FIGS. 10 and 11 enables the distal-end component to be an injection-moldable item of a softer elastomeric material (e.g., in the range 50 to 70 durometer hardness and preferably about 60-durometer hardness) while the remaining proximally extending component may be of stiffer elastomeric material (e.g., about 80-durometer hardness. Also, for greater radiation-viewing of an ET position in the patient's anatomy, a radio-opaque filler, typically 10 percent barium, as an ingredient mixed with the injection or otherwise molded distal-end component 31, will enable easy identification of ET location, upon radiographic inspection after ET insertion into the patient's trachea.

It will further be seen that for the preferred reducing-taper embodiment of FIG. 1, the construction of tube 10 with a roughly triangular cross-section throughout all of the distal part of the tapering length of the ET tube, and in imitation of the shape of the laryngeal opening, can be such that the vocal cords lie comfortably against walls of the larynx irrespective of the depth to which the ET device is inserted; the triangular, and thus anatomically conforming tube cross-section, opens the possibility of establishing an effective seal, by the close fit of the vocal cords against the distal walls of the ET tube, thus obviating the need for an inflatable cuff. Nevertheless, the use of a distally tapering section throughout the region of ET tube penetration into the trachea is a feature that is not necessarily limited to the preferred triangular section of the distal end of the ET tube. relatively soft elastomeric material, suitably injection-molded, and butt-welded or otherwise secured to the distal end of a second flexible proximal-end component 38 of relatively harder elastomeric material, which may nevertheless be so flexible as to be initally straight but able to adapt itself readily to the curved path of relatively rigid guidance provided by an intubating LMA. Thus, the flexible component 38 may be cylindrical throughout, for conformance with the rigid curvilinear guidance path of the intubating LMA, and at the welding 33 of both components 37, 38 to each other, the cylindrically tubular nature of both components 37, 38 at their interconnection may be of matching or suitably mating cylindrical nature.

The structure of FIG. 12 can be seen as of cylindrical-tube configuration to and through the welded connection 33, and therefore as having cylindrical consistency about a central axis or mid-line c, wherein the convergent distally projecting end is sufficiently rounded and continuous as to contain the mid-line or axis c, despite the fact of a shallow-angle truncation at 39; truncation 39 will be understood to account for a first side port (39), approximately 180° removed from the angular location, about axis c, for a second side port 39. Thus, the smoothly continuous contouring of the reduced distal end, about the local mid-line or axis c will be seen as favoring smooth non-traumatising entry into the glottic opening and into the trachea, even though the openings 39, 40 are differently located and asymmetrically profiled. Finally, as in FIG. 10, a safety sleeve 34 in FIG. 12 is circumferently bonded to components 37, 38 at spaced locations and straddling the connection 33.

What is claimed is:

1. An endotracheal tube extending from a proximal end to a distal end, the endotracheal tube including a proximal tube component, a distal cap component, and an inflatable sleeve, the proximal tube component defining the proximal end, the distal cap component defining the distal end, a first portion of the sleeve being sealed to the distal cap component at a first sleeve end, a second portion of the sleeve being sealed to the proximal tube component at a second sleeve end, and the distal cap component being formed at the first sleeve end from a material that is different from and softer than a material used to form the proximal tube component at the second sleeve end.

2. An endotracheal tube according to claim 1, the proximal tube component defining a central axis, the central axis intersecting a distal tip of the tube.

3. An endotracheal tube according to claim 1, the distal cap component being characterized by a durometer in the range of 50 to 70.

4. An endotracheal tube according to claim 1, the proximal tube component being characterized by a durometer of greater than 70.

5. An endotracheal tube according to claim 1, the proximal tube component being cylindrical.

6. An endotracheal tube according to claim 1, the proximal end being adapted for connection to an external source of air/gas supply for anesthetic service of a patient's lungs.

7. An endotracheal tube according to claim 1, the tube including a segment extending from a first location to a second location, the first location being spaced apart from the proximal end by a first distance, the second location being spaced apart from the proximal end by a second distance, the first distance being smaller than the second distance, the segment being characterized by a generally triangular cross-section.

8. An endotracheal tube extending from a proximal end to a distal end, the endotracheal tube including a proximal tube component, a distal cap component, and an inflatable sleeve, the proximal tube component defining the proximal end, the distal cap component defining the distal end, a first portion of the sleeve being sealed to the distal cap component at a first sleeve end, a second portion of the sleeve being sealed to the proximal tube component at a second sleeve end, the distal cap component being formed at the first sleeve end from a material that is different from and softer than a material used to form the proximal tube component at the second sleeve end;

wherein the tube includes a segment extending from a first location to a second location, the first location being spaced apart from the proximal end by a first distance, the second location being spaced apart from the proximal end by a second distance, the first distance being smaller than the second distance, the segment being characterized by a generally triangular cross-section; an outer perimeter of the tube at the first location being greater than the outer perimeter of the tube at the second location, the outer perimeter of the tube at any intermediate location between the first and second locations being greater than or equal to the outer perimeter of the tube at any location between the intermediate location and the second location.

9. An endotracheal tube extending from a proximal end to a distal end, the tube including a segment extending from a first location to a second location, the first location being spaced apart from the proximal end by a first distance, the second location being spaced apart from the proximal end by a second distance, the first distance being smaller than the second distance, the segment being characterized by a generally triangular cross-section, an outer perimeter of the tube at the first location being greater than the outer perimeter of the tube at the second location, the outer perimeter of the tube at any intermediate location between the first and second locations being greater than or equal to the outer perimeter of the tube at any location between the intermediate location and the second location, the distal end being insertable through a patient's mouth and into the patient's trachea while the proximal end remains outside the patient's mouth.

* * * * *